United States Patent [19]

Maxwell

[11] Patent Number: 5,201,772
[45] Date of Patent: Apr. 13, 1993

[54] SYSTEM FOR RESISTING LIMB MOVEMENT

[76] Inventor: Scott M. Maxwell, 250 Mercer St, #C317, New York, N.Y. 10012

[21] Appl. No.: 648,733

[22] Filed: Jan. 31, 1991

[51] Int. Cl.⁵ .......................... A61F 2/48; G09B 19/00
[52] U.S. Cl. .......................................... 623/24; 602/20; 434/258
[58] Field of Search ................ 602/19, 20; 128/24 R, 128/25 R; 434/258; 623/24

[56] References Cited

U.S. PATENT DOCUMENTS

| | | | |
|---|---|---|---|
| 4,078,670 | 3/1978 | Francois et al. | 623/24 X |
| 4,237,873 | 12/1980 | Terry et al. | 128/77 |
| 4,760,850 | 8/1988 | Phillips et al. | 128/432 W |
| 5,020,790 | 6/1991 | Beard et al. | 623/24 X |

FOREIGN PATENT DOCUMENTS 0380060  8/1990  European Pat. Off. .
WO85/04796 11/1985 PCT Int'l Appl. .

*Primary Examiner*—David Isabella
*Assistant Examiner*—Dinh X. Nguyen
*Attorney, Agent, or Firm*—Hamilton, Brook, Smith & Reynolds

[57] ABSTRACT

A six degree of freedom limb movement resistance system is described in which a linkage system of links and joints couples a fixed point in space to a movable end-point of the linkage. A limb coupling cuff is attached to the end point. Variable resistance force can be applied to the linkage via computer controls through a feedback path from position and velocity sensors. The linkage endpoint force acting to resist limb motion is in a direction opposite to the endpoint velocity vector.

14 Claims, 6 Drawing Sheets

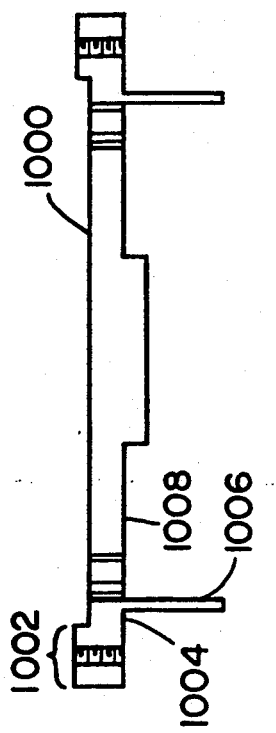
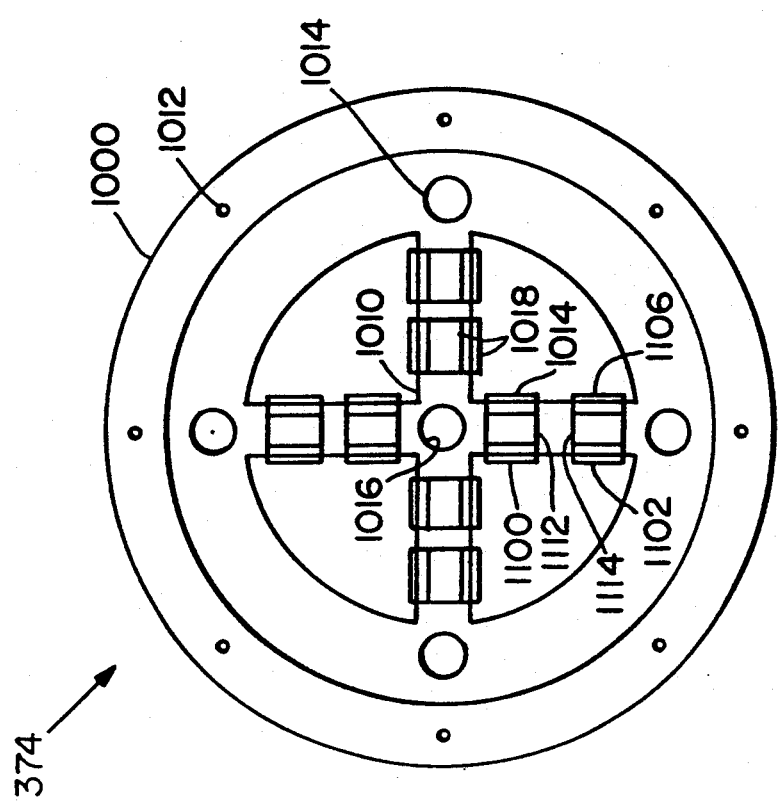
Fig. 10b
Fig. 10a

SYSTEM FOR RESISTING LIMB MOVEMENT

BACKGROUND ART

This invention was made with government support under contract Number H133E80024 awarded by the Department of Education. The government has certain rights in the invention.

Orthoses, or limb assistive devices, have been developed to assist disabled persons in performing daily functions. One application for such devices is in stabilizing limb motion in tremor patients.

The presence of random involuntary limb movement superimposed on purposeful limb movement is an abnormal condition that afflicts hundreds of thousands of patients suffering from a variety of diseases. Many tremor patients are disabled by these involuntary movements due to the fact that the amplitude of these movements is large enough to degrade or obscure voluntary movement attempted by the patient. Cerebral palsy patients suffering from athetosis may also be disabled by their involuntary limb movement. Chorea is another such condition.

In each of these cases, patients typically try to overcome the disability imposed by the involuntary movements of a particular limb, either by steadying the motion using an unafflicted limb, by jamming the afflicted limb against the body so as to restrict its vibration, or even by having another person grasp the limb to steady its motion. Drug therapies and surgery have been attempted with limited effectiveness and considerable risk for the patient.

However, in the past ten years or so, a number of orthoses have been developed for selectively suppressing random involuntary movements. These devices are based on the observation that significant reduction of the involuntary movements can be achieved by the application of viscous damping to the afflicted limb or body segment.

One such device is a one degree-of-freedom (DOF) orthosis with an electronically-controlled magnetic particle brake used to retard limb motion (See Dunfee, D. E., "Suppression of Intention Tremor by Mechanical Loading", M. S. Thesis, M. I. T. Department of Mechanical Engineering, Feb. 1979). This device, meant primarily for conducting experiments on the wrist, prevents the patient from performing whole-arm functional activities, since limb motion is rigidly constrained in the remaining DOF's.

Another prior art device is a 2 degree-of-freedom joystick used as a control interface to electrical devices (such as powered wheelchairs) while applying a resistive load to the limb. This system also cannot be used for whole-arm movements and is not meant as a general purpose functional orthosis.

Despite such work, a need exists for an orthosis which will enable full-arm movement, which requires six degrees of freedom in a safe and reliable manner. Such a device would be useful not only for tremor suppression, but would also find application in physical therapy and exercise machines, especially if the device were capable of achieving force-velocity colinearity. Force-velocity colinearity occurs when a force is applied to a device endpoint and the device moves in the direction of the force; resulting in a natural cause and effect result.

SUMMARY OF THE INVENTION

The invention consists of a system for resisting the motion of a subject's limb about six DOF's, and comprises a passive manipulator that can be used in conjunction with a microcomputer, a display monitor and electronic circuitry to process manipulator outputs for use by the microcomputer. The manipulator comprises a plurality of links, joined together by revolute joints to form a linkage system between a fixed point in space and a movable endpoint of the linkage. As the endpoint of the linkage is moved by the subject's limb, the joints of the linkage—and hence, the links themselves—rotate.

The rotation of certain joints in the linkage are resisted by a plurality of brakes (such as particle brakes). These joints allow translational motion of the endpoint in three DOF's and rotational motion of the endpoint about each of three mutually orthogonal axes. The limb (an arm) is coupled to the manipulator endpoint by a limb coupling cuff, the motion of the limb is resisted in six DOF's (three translational, three rotational).

The manipulator endpoint force acting to resist the arm motion is in a direction opposite the endpoint velocity vector, resulting in substantial force-velocity colinearity (FVC). FVC is attained when the force the human arm imparts is in the same direction as the desired movement.

BRIEF DESCRIPTION OF THE DRAWINGS

FIGS. 10a and 10b are the top view and cross-sectional views, respectively, of the elastic element and strain gauges of the force-torque sensor.

DETAILED DESCRIPTION OF THE INVENTION

Figure 1:
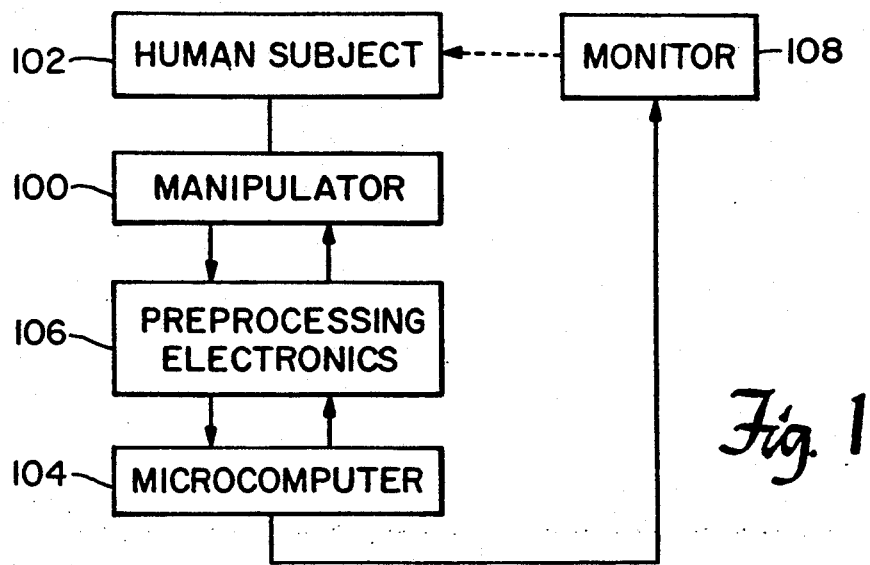
FIG. 1 is a block diagram of an example therapeutic system in which the manipulator of the invention may be used.

A preferred embodiment of the invention will now be described in connection with FIG. 1. This embodiment illustrates a six DOF device coupled to an arm of a subject. However, it is to be understood that the invention is not limited thereto and may in fact have greater or fewer DOF's and may be useful for coupling to other limbs. Also, it should be noted that while the term "manipulator" is used for convenience, the system is passive and the subject does the "manipulating". The system only restrains or resists forces exerted by the subject's limb. The manipulator 100 of the invention is one component in a physical therapeutic system comprised of (1) the manipulator 100; (2) a human subject 102; (3) a microcomputer 104 primarily used to process data and adjust resistive forces within the manipulator; (4) electronics 106 to preprocess data from the manipulator destined for the computer; and (5) a computer monitor 108 to display a moving object.

Figure 2:
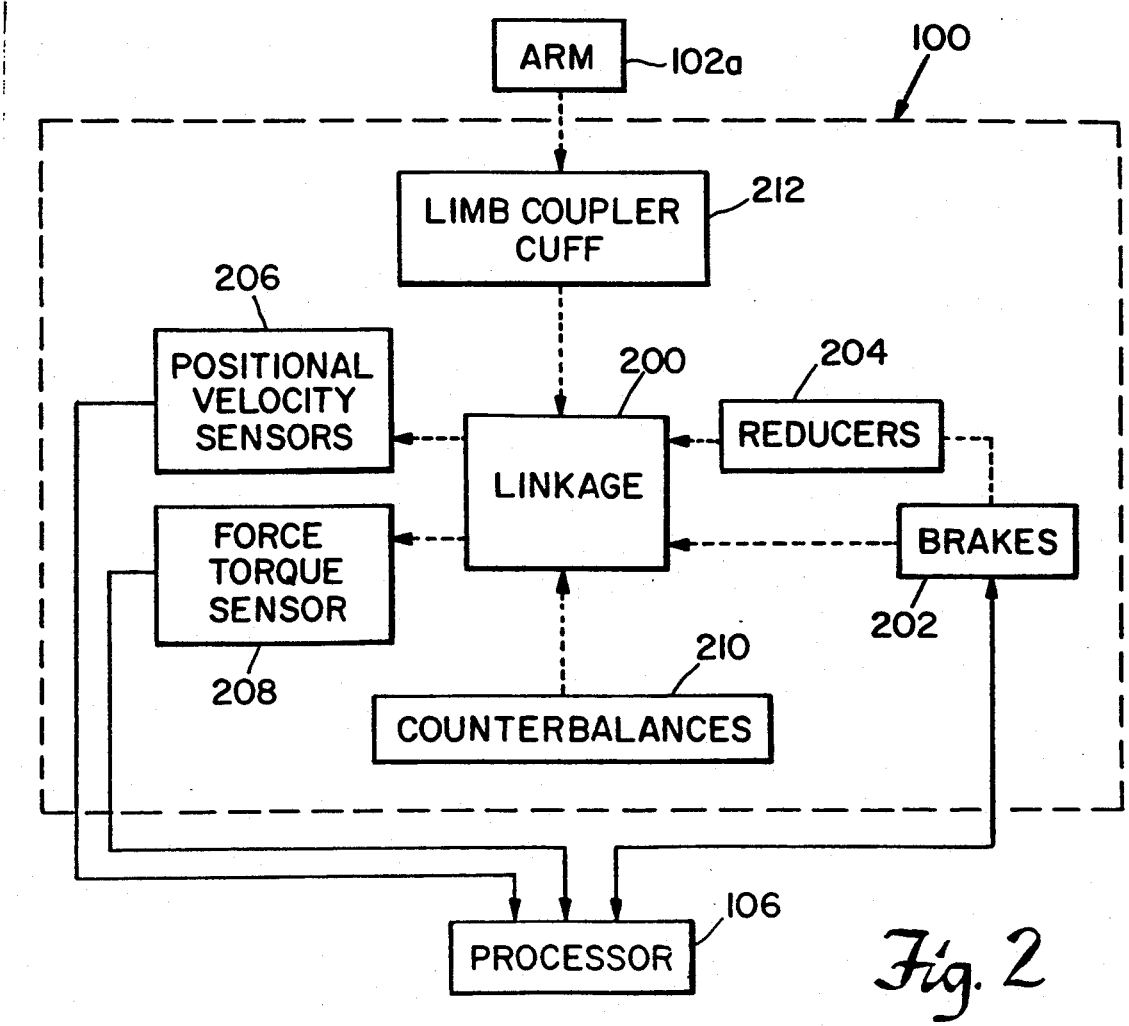
FIG. 2 is a block diagram of the manipulator of the invention.

The manipulator 100 is shown in the block diagram of FIG. 2 wherein mechanical connections are shown in dotted/dashed lines and electronic connections in solid. A linkage set 200, is mechanically coupled to brakes 202 which restrain the motion of certain joints in the linkage 200. Reducers 204 amplify the torques produced by the brakes 202. Position and velocity sensors 206 measure the angles about which certain joints have been rotated and the angular velocities, respectively. A force-torque sensor 208 yields measurements of loads applied at the manipulator endpoint. Counterbalances 210 compensate load imbalances about certain joints and a limb coupling cuff 212 couples the arm 102a to the manipulator endpoint. Each of these components will now be described in detail in the following sections:

I. Linkage

Figure 3:
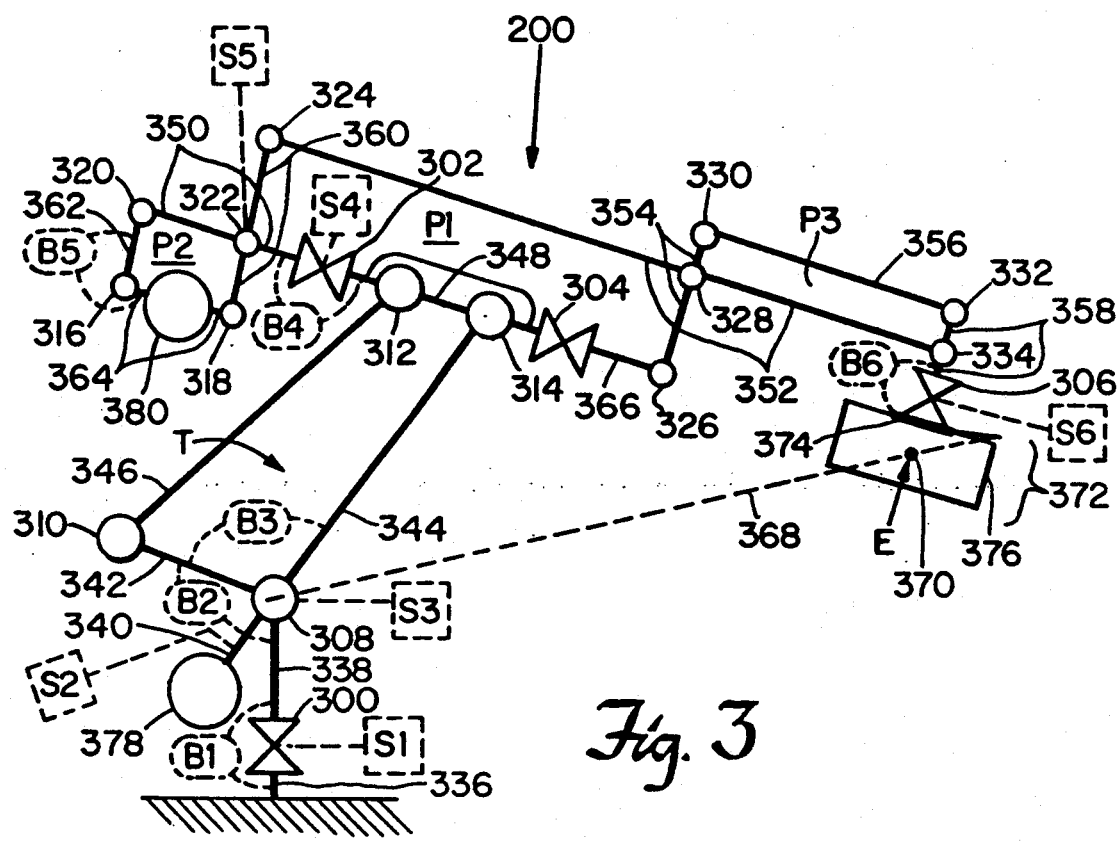
FIG. 3 depicts the links, joints, force-torque sensor, limb coupling cuff and counterbalance weights comprising the manipulator linkage.

The manipulator linkage 200 of FIG. 3 comprises a set of 15 aluminum tubes or 'links' 338–366 joined together by 18 revolute joints 300–334 that allow rotation of the links with respect to one another. In the figure, the butterfly-shapes (⋈) 300–306 represent one of four joints having rotation axes lying in the plane of the paper, while circles (O) 308–334 denote one of fourteen joints having rotation axes normal to the plane of the paper.

Figure 4:
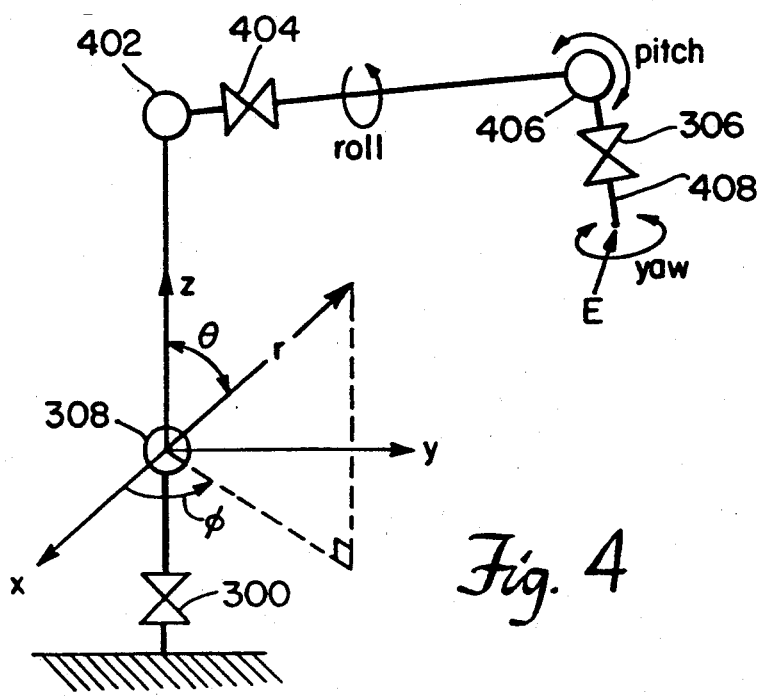
FIG. 4 is a dynamic equivalent of the manipulator linkage shown in FIG. 3.

The composite linkage structure 200 permits motion in six DOF's. The 6 DOF motion is more clearly seen in the simplified dynamic equivalent of FIG. 3, shown in the manipulator linkage drawing of FIG. 4. In FIG. 4, the rotation of joint 300 about its axis produces rotation in the $\pm\phi$ directions of a standard spherical coordinate system centered at joint 308. Joints 308 and 402 are coupled by a trapezoidal linkage T (shown in FIG. 3, but not in FIG. 4). Rotation of the coupled structure 308, 402, T about joint 308 causes rotation of the manipulator linkage in the $\pm\theta$ directions, and a combination of rotations of joints 308 and 402 causes translational movement in approximately the $\pm r$ directions. Hence, joints 300, 308 and 402 are responsible for positioning the manipulator endpoint in three dimensional space. Note that the manipulator endpoint E, defined as being the point at which the manipulator linkage 200 is coupled to the limb of the subject 102, roughly corresponds to the distal end of link 408 of FIG. 4.

Joints 404, 406 and 306 are used to change the orientation of the manipulator endpoint E. Rotation about the axis of the joints 404, 406, 306 corresponds to rotation about each of three mutually orthogonal axes of a coordinate system centered at joint 406. In other words, rotation of joint 404 produces roll motion at the endpoint, rotation of joint 406 produces pitch motion at the endpoint, and rotation of joint 306 produces yaw motion at the endpoint.

The more complicated structure of FIG. 3 is the linkage structure that is preferred in the present embodiment because of several practical limitations that arise in the simpler six-joint structure of FIG. 4. For example, it is difficult to obtain a rotationally-stiff system with the simpler design. Size and weight limitations are also present, and the system of FIG. 4 would suffer from backlash and chordal speed variation.

To overcome these limitations, a number of auxiliary joints 302, 310, 312, 316–332 that are not present in the FIG. 3 structure are introduced in the FIG. 4 structure. While joints 300, 306 and 308 of FIG. 4 correspond to single joints designated by the same reference numbers as in FIG. 3, joints 402, 404 and 406 of FIG. 4 are implemented by sets of joints in FIG. 3. Specifically, joint 402 corresponds to a coupling of joints 308–314, joint 404 corresponds to the pair of joints 302 and 304 and joint 406 corresponds to the set of joints 316–334.

Referring back to FIG. 3, link 336 is used to couple the entire manipulator structure (and in particular, joint 300) to a fixed external surface, such as a floor. Link 338 couples joints 300 and 308 together. Joint 308 is part of a trapezoidal four-bar linkage T comprising the four links 342–348 with joints at the vertices (i.e., connecting pairs of adjacent links in the trapezoid). Namely, joints 308 and 314 connect link pairs 342, 344 and 344, 348 respectively, while joints 310 and 312 connect pairs 342, 346 and 346, 348 respectively. As the four joints 308–314 rotate together appropriately, the shape of the trapezoid is changed, thereby causing the manipulator endpoint E to travel in approximately the $\pm r$ direction of a spherical coordinate system centered at joint 308 (i.e., along the dotted line 368). The current $\pm r$ direction is determined by the values of the azimuth and elevation angles $\phi$ and $\theta$ as determined by the amounts that joints 300 and 308 have been rotated.

The remaining links and joints of the manipulator of FIG. 3 constitute a novel gimbal link geometry referred to as the 'upper linkage,' which provides the three orientational DOF's corresponding to joints 404, 406 and 306 of FIG. 4. The upper linkage comprises three parallelograms $P_1$, $P_2$, $P_3$ of links and joints. In the central parallelogram $P_1$, joints 302 and 304 are coupled to either end of the trapezoidal linkage's link 348, with both joints providing a roll motion for the upper linkage. Attached to the other side of joint 302 is link 350, which joins with link 360 at joint 322. Attached to the other side of joint 304 is link 366, which meets link 354 at joint 326. The fourth side of the central parallelogram $P_1$ consists of link 352, which is attached to link 360 at joint 324 and to link 354 at joint 328.

The left parallelogram $P_2$ consists of links 350, 360, 362 and 364 and joints connecting adjacent pairs of these links. Specifically, pairs of links 350 and 362, 362 and 364, 364 and 360, and 360 and 350 are joined by joints 320, 316, 318 and 322, respectively. Note that links 350 and 360 of the left parallelogram $P_2$ are merely extensions of the same links of the central parallelogram $P_1$. Finally, the upper right vertex of the left parallelogram is coupled to the lower left vertex of the central parallelogram $P_1$ at joint 322.

The right parallelogram $P_3$ has as its sides links 352, 354, 356, and 358 and joints connecting adjacent pairs of these links. Specifically, pairs of links 352 and 354, 354 and 356, 356 and 358, and 358 and 352 are joined by joints 328, 330, 332 and 334, respectively. Note that links 352 and 354 of the right parallelogram $P_3$ are merely extensions of the same links of the central parallelogram $P_1$. Finally, the lower left vertex of the right parallelogram $P_3$ is coupled to the upper right vertex of the central parallelogram $P_1$ at joint 328.

The upper linkage in FIG. 3 simulates the function of joint 406 in FIG. 4 in that it produces a pitch motion in which the effective rotation is about a rotation axis 370 (point E) located at the intersection of links 366 and 372 if they were to be extended, and normal to the plane of the paper. The pitch motion is accomplished by deforming the parallelograms $P_1$, $P_2$, $P_3$ from rectangles to non-rectangles, with the deformation taking place as the joints 316-334 rotate in unison.

Finally, link 358 extends past joint 334 and couples with joint 306, which is responsible for producing a yaw motion. The other side of joint 306 is connected to link 372, which consists of the force-torque sensor 374 attached to the limb coupling cuff 376 worn by the subject.

II. Controlled Brakes

Six joints of the manipulator are coupled to controlled braking devices that resist manipulator endpoint motions imparted by the user in each of the six DOF's. The brakes for the DOF's corresponding to joints 300, 308 and 306 are labelled B1, B2 and B3, respectively, of FIG. 3 and are located near, and coupled to, the joints of FIG. 3 bearing the same reference numerals, while the brakes B4, B5, B6 for the DOF's corresponding to joints 306, 404 and 406 of FIG. 4 are located near joints 306, 302 and 316 of FIG. 3, respectively. The last three brakes are not near their respective joints but are instead located at other joints primarily because the alternate joint locations are better suited to provide counterbalancing (see Section VII).

A variety of braking mechanisms may be used to retard joint motion. These include electric motors, hydraulic actuators, mylar brakes, and magnetic particle brakes. In the present embodiment, magnetic particle brakes are used. The choice was motivated by the simplicity, reliability, low cost, and ease of computer control associated with such brakes.

Figure 5:
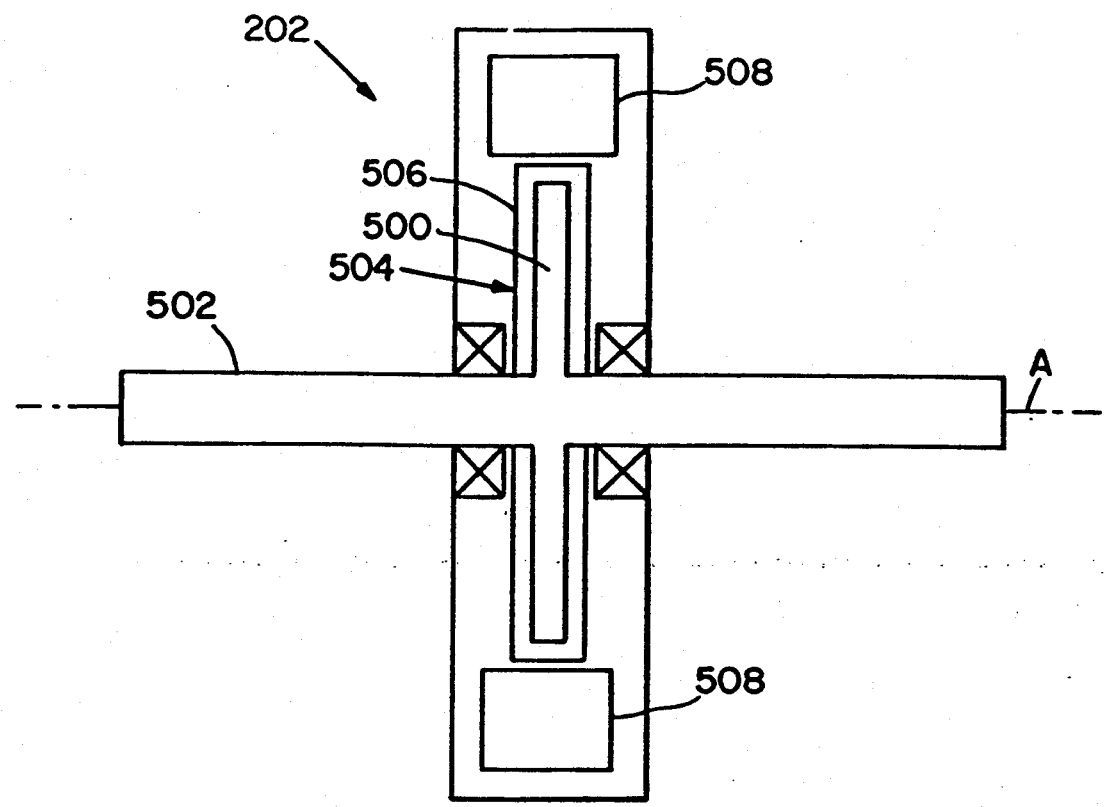
FIG. 5 is a schematic of a magnetic particle brake.

A typical magnetic particle brake B1 is shown in FIG. 5, to consists of a disk 500 that is attached to an output shaft 502. Note that in joints lacking reducers, the axis A of the output shaft 502 is the rotational axis of the joint (as will be seen in Section III). The disk 500 resides in a cylindrical cavity 504 larger than the disk. Powdered magnetic particles 506 are contained in the gap surrounding the disk 500. A coil of wire 508 is wound around the cylindrical cavity 504.

When an electrical current travels through the coil 508, a magnetic field parallel to the cylindrical axis of the disk 500 is produced in the cavity 504. The magnetic particles 506 in the gap align to form what resemble 'chains' in response to the magnetic field and these chains of particles 506 resist the motion of the disk 500 as it rotates along with the output shaft 502 to which it is attached, thereby retarding the rotation of the output shaft 502 about the axis A and making the joint stiffer. The particle brake has a resistive torque approximately proportional to the current applied to coil 508. The braking strength may therefore be controlled by varying the applied coil current.

Placid Industries B115P magnetic particle brake is a suitable brake for B1, B2 and B3, while model B15P may be used for brakes B4, B5, and B6. Models B115P and B15P have rated torques of 115 and 15 inch-lbs, respectively, at rated currents of $\frac{1}{3}$ and $\frac{1}{4}$ Amps, maximum speeds of 1800 and 2000 r.p.m., and a de-energized drag of 25 and 5 ounce-inches, respectively. The torque output of the first three brakes may be amplified using reducers, as described in the next section.

III. Reducers

Figure 6:
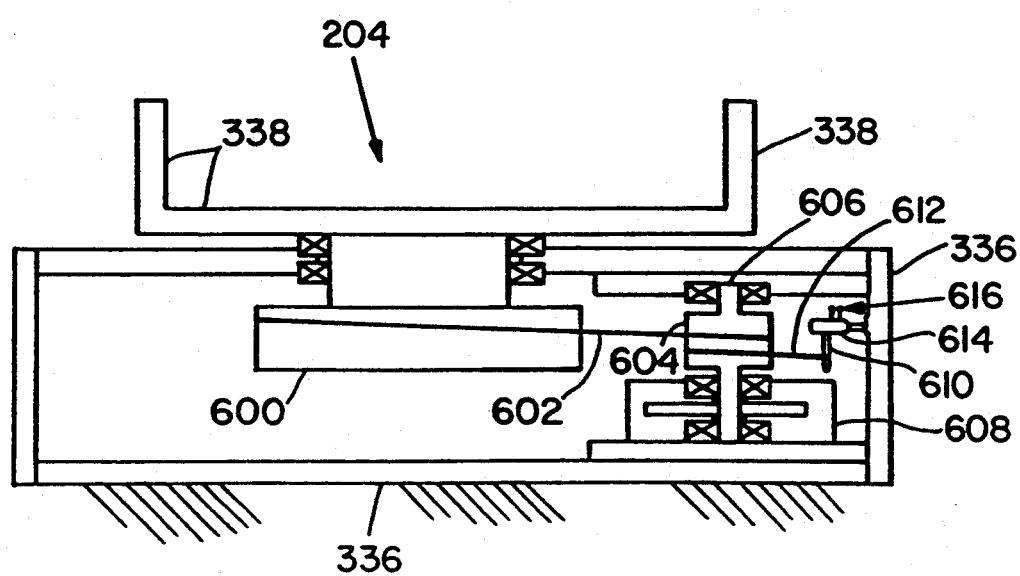
FIG. 6 is a schematic of the transmission for joint 300 of FIG. 3, depicting links, a particle brake, a reducer and a potentiometer.

Reducers 204 are used to amplify the torque output of particle brakes B1, B2, and B3 by approximately four times using cable drive transmissions. FIG. 6 illustrates an exemplary reducer transmission, i.e., the transmission for joint 300. A capstan 600, made of aluminum and having a diameter of about 8 inches, is attached to link 338 (of FIG. 3), and is coupled by a $\frac{1}{8}$ inch diameter nylon-covered aircraft cable 602 to a smaller diameter capstan 604, which has a diameter of 2 inches and is attached to the output shaft 606 of particle brake 1. The base 608 of particle brake B1 is attached to link 336 (also see FIG. 3). The rotation of link 338 occurs about a rotation axis that coincides with the axis of symmetry of large capstan 600, and is retarded with a resistive torque that is four times that produced by the particle brake, per se. A position sensor, described in more detail in Section IV, consisting of a potentiometer 614 with a rotatable tuning arm 610 is coupled by pulley 612 to capstan 606. Rotation of the output shaft 606 relative to the base 608 corresponds to a rotation of link 338 relative to link 336. The potentiometer tuning arm 610 of the position sensor therefore indicates the amount that joint 300 (see FIG. 3 between links 338 and 336) has been rotated.

Figure 7:
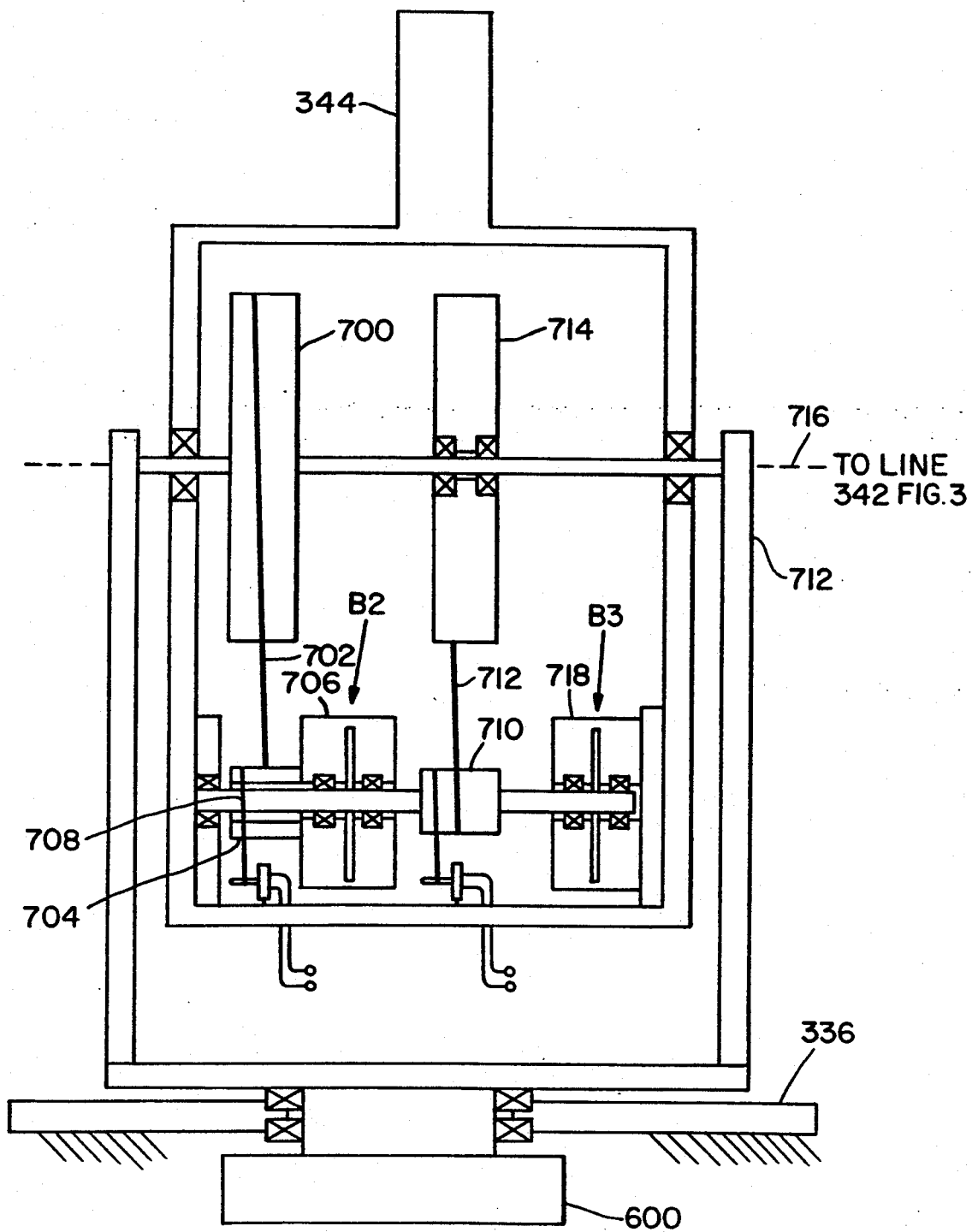
FIG. 7 is a schematic of the transmission for joints 308 and 314 of FIG. 3, depicting links, particle brakes, reducers and potentiometers.

FIG. 7 illustrates the more complicated cable drive transmissions that couple brakes B2 and B3 to the linkage. As seen in FIG. 7, joint 308 of FIG. 3 in fact consists of two joints, that correspond to the intersection of links 338 and 342 and the intersection of links 342 and 344 of FIG. 3.

Link 338 is attached to an 8 inch capstan 700, coupled by nylon-covered aircraft cable 702 to 2 inch capstan 704 which is attached to the base 706 of a particle brake B2. The output shaft 708 of particle brake B2 is attached to a 2 inch capstan 710, which is coupled by aircraft cable 712 to an 8 inch capstan 714 that is attached to link 342 of FIG. 3 (not shown in FIG. 7). Hence relative motion between the output shaft 708 and base 706 of particle brake B2 corresponds to relative motion between links 338 and 342 via the 2 inch capstans 704, 710 and 8 inch capstans 700, 714, with links 338 and 342 rotating about a rotation axis labelled 716 in the figure. Thus resistive torque produced by particle brake B2 is amplified via capstan pairs 704, 700 and 710, 714 to provide greater damping in the relative motion between links 338 and 342.

Link 344 is attached to the base 718 of particle brake B3. The output shaft 708 of particle brake B3, which coincides with the output shaft of particle brake B2, is likewise attached to 2 inch capstan 710, which is in turn coupled via aircraft cable 712 to the 8 inch capstan 714 attached to link 342 of FIG. 3 (not shown in FIG. 7). Consequently, relative motion between the output shaft 708 and base 718 of particle brake B3 corresponds to relative motion between links 342 and 344 via the 2 inch capstan 710 and 8 inch capstan 714, with links 342 and 344 rotating about rotation axis 716. Thus, resistive torque produced by particle brake B3 is amplified via capstan pair 710, 714 to provide greater damping in the relative motion between links 342 and 344.

IV. Position/Velocity Sensors

The six position/velocity sensors S1-S6, located near and coupled to the manipulator linkage joints 300, 308, 308, 304, 320 and 306 of FIG. 3, provide information as to the amounts that these joints have been rotated (i.e., position information) and how fast they are rotating (velocity information). The position/velocity sensors at the joints listed above correspond to the DOF's associated with joints 300, 308, 402, 404, 406 and 306 of FIG. 4, respectively, and are hereafter referred to as position/velocity sensors S1-S6, for convenience. Equivalently, position sensors S1-S6 indicate the angle between the following pairs of links: 336 and 338, 338 and 342, 338 and 344, 348 and 350, 350 and 360, and 358 and 372. The velocity sensors indicate the rate of change of these angles.

Figure 8:
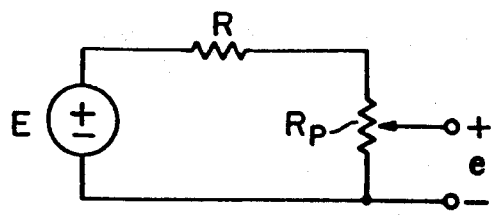
FIG. 8 is a schematic of the voltage divider circuit equipped with a potentiometer to measure position.

Referring back to FIG. 6, a position sensor consists of a 5K$\Omega$ potentiometer 614 (such as the Helipot model 6186-R5K L1.0 B604M potentiometer) having a tuning arm 610 coupled to the output shaft 606 of the joint by means of a pulley, so that the rotation of the output shaft 606 causes the tuning arm 610 of the potentiometer to rotate. This rotational action varies the resistance of the potentiometer as measured across two of its leads 616. The value of the resistance $R_P$ indicates the amount that the joint has been rotated. The resistance value is determined by connecting the potentiometer leads 616 to a voltage divider circuit comprising a voltage source E coupled in series with a standard resistor R and the potentiometer value $R_P$ (as shown in FIG. 8) and measuring the voltage $e = E\ R_p/R + R_p)$.

A velocity measurement is obtained by differentiating the measurement provided by the position sensor, using a well-known analog differentiator circuit. Joints other than the six joints mentioned, do not contribute to additional DOF's, therefore, additional potentiometers at these joints would provide no additional position and/or velocity information.

V. Force-Torque Sensor

Referring back to FIG. 3, the force-torque sensor (FTS) 374 is located at the manipulator endpoint E to measure the load applied by the limb coupling cuff 376 on the manipulator endpoint in each of the six DOF's. That is, three forces and three torques are measured. As will be shown in detail in connection with FIGS. 10-12, this measurement process consists of several distinct steps. First, a sensing element senses the deformation of an elastic element 1000 in response to an applied load. An electrical circuit (FIG. 12) converts the output of the sensing element into an electrical signal suitable for computer interfacing. Finally, a transformation is performed whereby the vector of electrical measurements is mapped to a vector whose elements are the applied forces and torques.

Shown in FIGS. 10a-10b is the elastic element 1000 machined from 7075-T6 aluminum alloy. The elastic element, has an overall diameter of 4 inches and an overall thickness of 0.8 inches. The element consists of four concentric annuli 1002-1008 (see FIG. 10b) having different thicknesses, and four spokes 1010 (see FIG. 10a) each being spaced at 90 degree intervals radiating outward from the center of the innermost annulus 1008. A number of holes 1012, 1014 are drilled into the elastic element. Holes 1012 and holes 1014 accommodate screws securing a FTS cover plate and a limb coupling cuff (not shown), respectively to the element 1000. Hole 1016 accommodates the output shaft of particle brake B6 (i.e., the brake coupled to joint 306).

Strain gauges 1018 attached to each of the spokes of the elastic element sense deformations of the element. Two groups (a vertical group and a horizontal group) of four strain gauges are attached to each spoke. In each group, each of the four gauges is attached to a different edge of the spoke (which has a square cross-section).

Figure 11A:
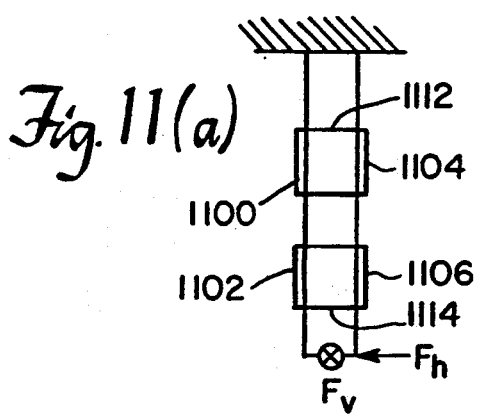
FIGS. 11a and 11b are the top and side views of the strain gauges on a single spoke of the elastic element.
Figure 11B:
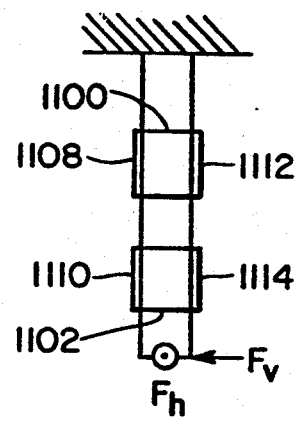
Figure 12A:
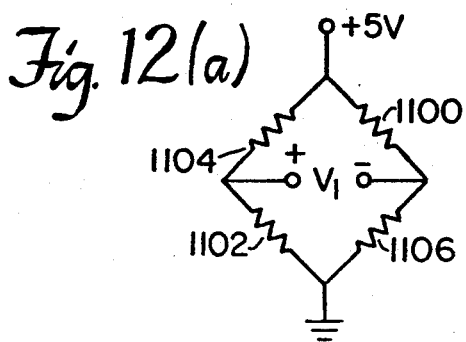
FIGS. 12a and 12b are schematics of the Wheatstone bridge circuits for the horizontal and vertical components of the applied load.
Figure 12B:
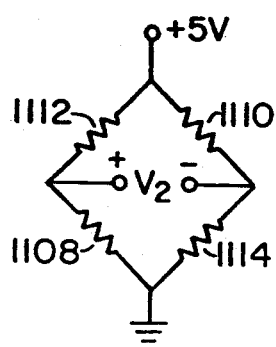

In addition to sensing deformations, the strain gauges also provide an electrical representation of the deformation. Specifically, each strain gauge has a nominal resistance of 120 $\Omega$ which varies with the sensed strain. Referring to FIG. 11, four strain gauges (a.k.a. variable resistors) 1100-1106, two from each group on a particular spoke, are electrically configured to form a Wheatstone bridge circuit (see FIG. 12). The voltage $v_1$ across the bridge is measured. A nonzero value of $v_1$ indicates unequal strain gauge resistance values. The remaining four strain gauges on the spoke 1108-1114 (again, two from each group) also provide a voltage, $v_2$, in a similar manner. The two measured voltages $v_1$ and $v_2$ provide information as to the horizontal and vertical components of the applied force, respectively. The strain gauges on the other three spokes provide this voltage information in the same way, therefore, a vector of voltages $v = [v_1\ v_2\ \ldots\ v_8]^T$ is obtained.

Finally, voltage vector v is converted to a force vector f via the transformation $$f = Cv,$$

where the first three elements of f are the measured values of the three orthogonal components of the applied force and the last three elements are the values of the components of the applied torque, and C is a 6×8 matrix whose elements were obtained through calibration using applied forces and torques of known magnitude.

VI. Limb Coupling Cuff

A limb coupling cuff, labelled 376 in FIG. 3, acts as the physical interface between the human limb (in the present application, the arm) and the manipulator, and has the function of transferring loads from the manipulator to the limb. Preferably, cuff 376 is made of plastic or plaster or styrofoam and molded to the shape of the limb. The goal of the cuff is to provide the stiffest, most solid connection between the manipulator and the limb, so that manipulator control over the limb is maximized, without substantially sacrificing user comfort. A handle which is gripped by the user can be used in place of the limb coupling cuff.

VII. Counterbalances

The load of the linkage structure described in Section I with the equipment of Sections II-VI, is unbalanced about the rotational axes of several joints. For example, in FIG. 3, the moment produced by the portion of the linkage (as equipped with particle brakes, reducers, position sensors, and the force-torque sensor) to the right of joint 314 exceeds the moment produced by the portion to the left, giving the manipulator arm the tendency to tilt downward on the right side. This effect causes the human subject to feel a weight load at the manipulator endpoint. At joint 308, a similar imbalance exists. Finally, the two upper parallelograms of the upper linkage do not balance the lower parallelogram about joint 304.

To balance the load about each of these rotational axes, counterbalance weights are placed at appropriate locations in the manipulator structure. First, certain particle brakes themselves act as counterbalances. Particle brakes B2 and B3 act as counterbalances for the rotational axis of joint 308, brakes B4 and B5 act as counterbalances for the rotational axis of joint 314, and brake B5 acts as a counterbalance for the rotational axis of joint 304. In addition, lead weights used solely for the purpose of counterbalancing supplement the particle brakes. Lead weights 378 and 380 attached to links 340 and 364 act to counterbalance loads about the rotational axes of joints 308 and joints 314 and 304, respectively.

Applications

In a general sense, the manipulator of the invention is a system for controllably resisting the movement of a limb. Accordingly, the manipulator can be used in a number of different applications.

Figure 9:
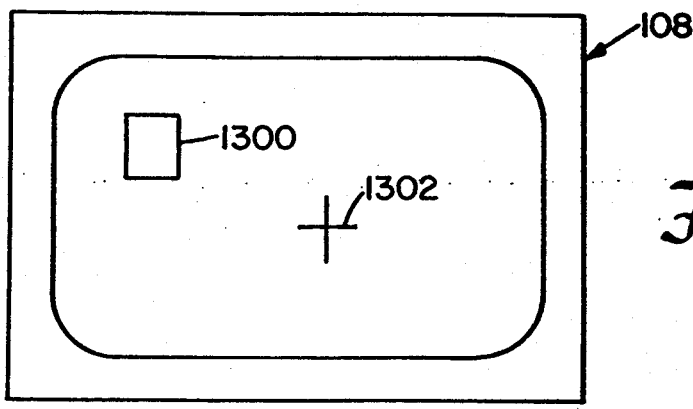
FIG. 9 illustrates the moving target and Manipulator crosshair that appear on the display monitor in the pursuit tracking task.

One such application is that in which the manipulator is used as an exercise machine. The microcomputer 104 of FIG. 1 is programmed to display a moving target 1300 on the display monitor 108, as shown in FIG. 9. Simultaneously, the subject 102 attempts to pursue the target 1300 by moving his/her arm, as indicated by a crosshair 1302 displayed on the monitor 108. The motion of the target can be programmed to correspond to certain arm movements, so that certain muscles can be exercised. Moreover, the amount of resisting force can be controlled by varying coil currents in the particle brakes so as to vary resistance levels in the exercise machine.

Another application of the manipulator is in physical therapy. Here, the manipulator would be used in conjunction with a microcomputer and display monitor as above, with the goal being the rehabilitation of certain muscles. Of course, in each of these applications, the use of the display monitor for pursuit tracking tasks is not necessary. The manipulator could be used in the manner that conventional weight-training and exercise machines are used.

Equivalents

This completes the description of the preferred embodiment of the invention. Those skilled in the art may recognize other equivalents to the specific embodiments described herein, which equivalents are intended to be encompassed by the claims attached hereto.

I claim:

1. A system for resisting limb movement comprising:
   (a) a plurality of links joined by joints to form a linkage system between a fixed point in space and a movable end point of said linkage system;
   (b) a limb coupler connected to said linkage system for coupling a limb to said end point; and
   (c) a plurality of brakes coupled to said linkage system for resisting translational link movement in at least three mutually orthogonal directions and for resisting rotational link movement about at least three mutually orthogonal axes.

2. The system of claim 1 further comprising means for moving the linkage system in a direction of a force being applied to said end point.

3. The system of claim 1 including a plurality of position sensors coupled to said linkage system for sensing the degree of translational and rotational movement of said links about said joints in the three directions and three axes.

4. The system of claim 3 including a plurality of velocity sensors coupled to said linkage system for sensing the rate of said translational and rotational movement.

5. The system of claim 4 including a computer wherein the sensed positions and rates generate signals which are coupled to at least one brake to vary the amount of resistance generated by the brake.

6. A system of claim 1 wherein the brake effects a resistance in a direction opposite to a direction of said movable endpoint.

7. A system of claim 1 wherein the linkage system further comprises at least three parallelograms of links and joints.

8. A system of claim 1 wherein the brake further comprises a first cylinder with a first diameter coupled to the brake, a second cylinder with a second diameter which is wider than said first diameter coupled to a rotating joint of the linkage system and a cable with one end connected to the second cylinder, said cable is wrapped around the first cylinder to amplify the brake torque.

9. A system of claim 8 wherein the brake further includes a position sensor, said sensor is connected to the end of the cable opposite to the end connected to the second cylinder.

10. A system of claim 9 wherein at least one brake is positioned on a linkage as a counterbalance weight.

11. A system for resisting limb movement comprising:
   a) a plurality of links joined by joints to form a linkage system including at least three parallelograms of links and joints between a fixed point in space and a movable end point of said linkage system;
   b) a limb coupler for coupling a limb to said end point;
   c) a plurality of brakes for resisting translational link movement in at least three mutually orthogonal directions and for resisting rotational link movement about at least three mutually orthogonal axes;
   d) a plurality of position sensors for sensing the degree of translational and rotational movement of said links about said joints in the three directions and three axes;
   e) a plurality of velocity sensors for sensing the rate of said translational and rotational movement;
   f) a first cylinder with a first diameter coupled to the brake;
   g) a second cylinder with a second diameter which is wider than said first diameter coupled to a rotating joint of the linkage system;
   h) a cable with one end connected to the second cylinder, said cable is wrapped around the first cylinder to amplify the brake torque; and
   i) a computer wherein the sensed positions and rates generate signals which are coupled to at least one brake to vary the amount of resistance generated by the brake.

12. A method for resisting limb movement comprising the steps of:
   a) coupling a limb to a movable end point of a linkage system, said linkage system including a plurality of links joined by joints to form a linkage system between a fixed point in space and said movable end point of said linkage system for movement in an end point velocity direction;
   b) sensing the degree of translation and rotation of said links;
   c) sensing the rate of translation and rotation of said links;

d) resisting translational link movements in at least three mutually orthogonal directions;
e) resisting rotational link movements about at least three mutually orthogonal axes; and
f) varying the translational resistances and the rotational resistances in accordance with the sensed positions and rates of movement of the links.

13. A method as recited in claim 12 wherein the translational and rotational resistors are effected in a direction opposite to the end point velocity direction.

14. A method as recited in claim 12 wherein the linkage system further comprises at least three parallelograms of links and joints.

* * * * *

UNITED STATES PATENT AND TRADEMARK OFFICE
CERTIFICATE OF CORRECTION

PATENT NO. : 5,201,772
DATED : April 13, 1993
INVENTOR(S) : Scott M. Maxwell

It is certified that error appears in the above-indentified patent and that said Letters Patent is hereby corrected as shown below:

Col. 12, line 1, delete "resistors" and insert --resistances--.

Signed and Sealed this

Fifth Day of April, 1994

Attest:

BRUCE LEHMAN

*Attesting Officer*    Commissioner of Patents and Trademarks